United States Patent [19]

Aoyagi

[11] Patent Number: 4,466,962
[45] Date of Patent: Aug. 21, 1984

[54] INSECTICIDAL 1-ALKYL-5-SUBSTITUTED-4-CHLOROPYRAZOLE-3-YL-(THIO)PHOSPHATES AND (THIO)PHOSPHONATES

[75] Inventor: Edward I. Aoyagi, Petaluma, Calif.

[73] Assignee: Chevron Research Company, San Francisco, Calif.

[21] Appl. No.: 470,823

[22] Filed: Feb. 28, 1983

[51] Int. Cl.³ .................... A01N 57/16; C07F 9/65
[52] U.S. Cl. ........................... 424/200; 548/116
[58] Field of Search .................... 548/116; 424/200

[56] References Cited

U.S. PATENT DOCUMENTS 3,825,557  7/1974  Hoffmann et al. ............ 548/116 X

Primary Examiner—Richard Raymond
Attorney, Agent, or Firm—S. R. LaPaglia; T. G. DeJonghe; S. L. Biggs

[57] ABSTRACT

1-Alkyl-5-substituted-4-chloropyrazole-3-yl-(thio)phosphates and (thio)phosphonates of the formula

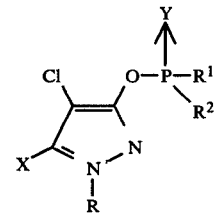

wherein R is lower alkyl; $R^1$ is lower alkoxy; $R^2$ is lower alkyl or lower alkoxy; X is chloro or the group $-SR^3$ wherein $R^3$ is lower alkyl; and Y is sulfur or oxygen are insecticidal, and are particularly effective against cabbage looper.

24 Claims, No Drawings

INSECTICIDAL 1-ALKYL-5-SUBSTITUTED-4-CHLOROPYRAZOLE-3-YL-(THIO) PHOSPHATES AND (THIO) PHOSPHONATES

BACKGROUND OF THE INVENTION

This invention is drawn to novel compounds which have insecticidal activity.

With the world more dependent for food on less and less acreage of land, it is necessary to develop insecticides which effectively protect the crops from destruction and/or damage by insect pests United Kingdom patent application GB No. 2,013,182A discloses the use of 1 or 2-alkyl-5-substituted pyrazoles as insecticides, acaricides and nematocides.

U.S. Pat. No. 3,952,098 discloses pyrazolo(thiono)-phosphoric acid esters as insecticidal.

United Kingdom Pat. No. 1,535,498 and U.S. Pat. No. 4,163,052 disclose pyrazolyl-(thio)phosphates (thio)-phosphonates and phosphoramides useful as insecticides, acaricides and nematocides.

SUMMARY OF THE INVENTION

The 1-alkyl-5-substituted-4-chloropyrazole-3-yl-(thio)phosphates and (thio)phosphonates of this invention are represented by the formula

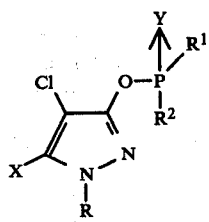

I wherein R is lower alkyl, $R^1$ is lower alkoxy, $R^2$ is lower alkyl or lower alkoxy; X is chloro or the group $-SR^3$ wherein $R^3$ is lower alkyl; and Y is sulfur or oxygen.

Among other factors, this invention is based upon my finding that the compounds of this invention possess surprisingly good insecticidal activity against a variety of insects. These compounds also are especially effective against certain lepidopterans, such as cabbage looper as well as other insects such as houseflies, cotton aphids and alfalfa weevils. In addition, some of the compounds are particularly effective against Acarines, such as *Tetranychus urticae*.

In part due to their superior insecticidal activity, preferred lower alkyl R groups include, for instance, methyl, ethyl, isopropyl, n-hexyl and the like. Particularly preferred R groups are ethyl and methyl. Most preferably R is methyl.

Preferred $R^2$ lower alkyl groups include methyl and ethyl.

Preferred R' and $R^2$ lower alkoxy groups include methoxy and ethoxy.

Preferred $R^3$ lower alkyl groups include, for instance, methyl, ethyl, n-propyl, isopropyl, n-hexyl and the like. Particularly preferred $R^3$ groups include ethyl, methyl, n-propyl and isopropyl.

DEFINITIONS

As used herein the following terms have the following meanings, unless expressly stated to the contrary.

The term "alkyl" refers to both straight- and branched-chain alkyl groups. The term "lower alkyl" refers to both straight- and branched-chain alkyl groups having a total from 1 through 6 carbon atoms and includes primary, secondary and tertiary alkyl groups. Typical lower alkyls include, for example methyl, ethyl, n-propyl, isopropyl, n-butyl, t-butyl, n-hexyl and the like.

The term "halo or halogen atom" refers to the groups fluoro, chloro, bromo and iodo.

The term "alkoxy" refers to the group $R^1O-$ wherein $R^1$ is alkyl.

The term "lower alkoxy" refers to alkoxy groups having from 1 through 6 carbon atoms and includes, for example, methoxy, ethoxy, t-butoxy, hexoxy and the like.

The term "alkylthio" refers to the R"S— group, where R" is lower alkyl.

The term "pyrazole" refers to the

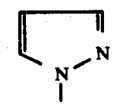

group. The conventional numbering system for this group is shown below.

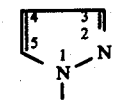

DETAILED DESCRIPTION OF THE INVENTION

The compounds of this invention wherein $R^2$ is lower alkoxy and X is $-SR^3$ are conveniently prepared according to the following scheme:

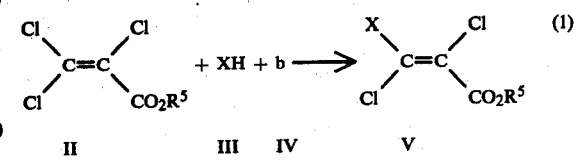

(1)

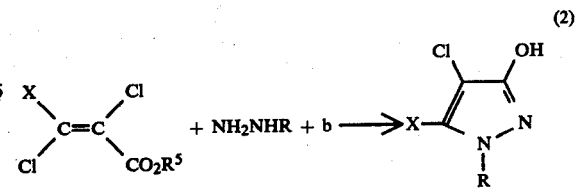

(2)

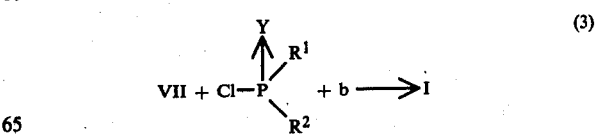

(3)

wherein R, $R^1$, $R^2$, $R^3$, X, and Y are as defined in conjunction with formula above; b is an organic or inorganic base; and $R^5$ is lower alkyl.

Reaction (1) is conducted by adding an essentially equimolar amount of III to II. An essentially equimolar amount of a base, b, is added to the reaction to scavenge the acid generated. Either organic or inorganic bases may be employed. Preferably, an organic base such as trialkylamine (e.g., triethylamine), pyridine and the like is employed. The reaction is conducted in the liquid phase employing an inert organic solvent such as methanol, ethanol, tetrahydrofuran, and the like. The reaction is exothermic and cooling may be necessary. The reaction is generally conducted from 0°-50° C., although preferably at from 20°-35° C. Reaction pressure is not critical and for convenience, reaction pressure is atmospheric. The reaction is generally complete within 1-24 hours. The product, VI, is isolated by conventional procedures such as extraction, filtration, chromatography, distillation, or alternatively, used in Reaction (2) without purification and/or isolation.

Reaction (2) is conducted by adding an essentially equimolar amount of an alkyl hydrazine, VI, to V using an equimolar amount of a base, b, to yield the pyrazole, VII. The reaction is conducted in the liquid phase using an inert organic solvent such as benzene, toluene, tetrahydrofuran, and the like. A base is employed to scavenge the acid generated in the reaction. Either an organic or inorganic base may be used. Suitable organic bases include, for instance, trialkylamines, pyridine, and the like. Suitable inorganic bases include sodium bicarbonte, potassium carbonate, sodium carbonate, and the like. Preferably, an inorganic base such as potassium carbonate, sodium carbonate, potassium bicarbonate, and the like, is employed. The reaction is exothermic and cooling may be necessary during addition of the reagents. The reaction is generally conducted from 0°-110° C. and is generally complete within 1-24 hours. Reaction pressure is not critical and for convenience, atmospheric pressure is used. The resulting pyrazole, VII, is isolated by conventional procedures such as extraction, filtration, chromatography, crystallization, or alternatively used in Reaction (3) without purification and/or isolation.

Reaction (3) is conducted by adding essentially equimolar amounts of either dialkoxychlorothiophosphate or dialkoxychlorophosphate, VIII, to VII. The reaction is conducted in the liquid phase using an organic solvent such as methyl ethyl ketone, acetone, dimethoxyethane, chloroform, and the like. Between 1 and 2 equivalents of an organic or inorganic base is added to the system to scavenge the acid generated by the reaction. Preferably, an inorganic base such as potassium carbonate, potassium bicarbonate, and the like, is used. Reaction pressure is not critical and for convenience, the reaction pressure is generally atmospheric. The reaction is heated at reflux and is generally complete within 1-24 hours. The product, I, is isolated by conventional procedures such as extraction, filtration, chromatography, and the like.

The compounds of this invention wherein $R^2$ is lower alkoxy and X is chloro are conveniently prepared by starting with the appropriate acryloylalkyl ester V and following reactions (2) and (3).

The compounds of this invention where $R^2$ is lower alkyl are conveniently prepared by treating intermediate VII, prepared as described according to the following synthetic scheme:

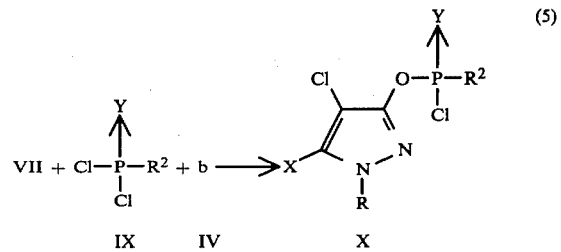

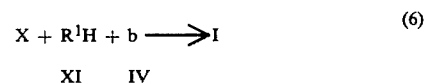

wherein R, $R^1$, $R^2$, X, Y and b are as previously defined.

Reaction (5) is conducted by adding essentially equimolar amounts of IX and IV to VII. Suitable bases, IV, include organic and inorganic bases such as triethylamine, pyridine, potassium carbonate, and the like. The reaction is conducted in the liquid phase using an organic solvent such as methyl ethyl ketone, acetone, dimethoxyethane, chloroform, and the like. Reaction pressure is not critical and, for convenience, the reaction is carried out at ambient pressure. The reaction is generally conducted at a temperature of about 0° C. to about 50° C., and for convenience may be carried out in the temperature range of about 20° C. to about 35° C. The reaction generally is complete within about 1 to about 24 hours. The product is isolated by conventional procedures such as extraction, filtration, chromatography, or alternativey used in Reaction (6) without purification and/or isolation.

Reaction (6) is conducted by adding approximately equimolar amounts of XI and IV to X. Suitable bases IV include organic and inorganic bases such as triethylamine, pyridine, potassium carbonate, and the like. The reaction is conducted in the liquid phase using an organic solvent such as methyl ethyl ketone, acetone, dimethoxyethane, chloroform, and the like. Reaction pressure is not critical and, for convenience, the reaction is carried out at ambient pressure. The reaction is generally conducted at a temperature of about 20° C. to about 100° C.; and, for convenience, it may be conducted at ambient temperature. The product, I, is isolated by conventional procedures such as extraction, filtration, chromatography, and the like.

UTILITY

The compounds of this invention are useful for controlling insects, particularly against such insects as cabbage looper [*Trichophisia ni* (Hubner)]. However, some insecticidal compounds of this invention may be more insecticidally active than others against particular pests.

Like most insecticides, they are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hosts susceptible to insect attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5% to 80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in insecticidal formulations include, for example, the alkyl and alkylaryl sulfonates and sulfonates and their sodium salts; alkylamide sulfonates, including fatty methyl taurides; alkylaryl polyether alcohols, sulfated higher alcohols, and polyvinyl alcohols; polyethylene oxides; sulfonated animal and vegetable oils, sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the pesticidal composition.

Dusts are freely flowing admixtures of active ingredient with finely divided solids such as talc, natural clays, kieselguhr, pyrophyllite, chalk, diatomaceous earths, calcium phosphates, calcium and magnesium carbonates, sulfur, lime, flours, and other organic and inroganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogeneous liquid or paste compositions which are readily dispersed in water or other dispersants, and may consist entirely of the toxicant with a liquid or solid emulsifying agent, or may also contain a liquid carrier, such as xylene, heavy aromatic napththas, isophorone, and other non-volatile organic solvents. For application, these concentrates are dispersed in water or other liquid carrier, and normally applied as a spray to the area to be treated.

Other useful formulations for insecticidal applications include simple solutions of the active ingredient in a dispersant in which it is completely soluble at the desired concentration, such as acetone, alkylated naphthalenes, xylene, or other organic solvents. Granular formulations wherein the toxicant is carried on relatively coarse particles, are of particular utility for aerial distribution or for penetration of cover-crop canopy. Baits, prepared by mixing solid or liquid concentrates of the toxicant with a suitable food, such as a mixture of cornmeal and sugar, are useful formulations for control of insect pests. Pressurized sprays, typically aerosols wherein the active ingredient is dispersed in finely divided form as a result of vaporization of a low-boiling dispersant solvent carrier, such as the Freons, may also be used. All of these techniques for formulating and applying the active ingredient are well known in the art.

The percentages by weight of the toxicant may vary according to the manner in which the composition is to be applied and the particular type of formulation, but in general comprises 0.1% to 95% of the toxicant by weight of the insecticidal composition.

The insecticidal compositions may be formulated and applied with other active ingredients, including nematocides, insecticides, fungicides, bactericides, plant growth regulators, fertilizers, etc. In applying the chemical an effective amount and concentration of the toxicants of this invention is, of course, employed.

The terms "insecticide" and "insect" as used herein refer to their broad and commonly understood usage rather than to those creatures which in the strict biological sense are classified as insects. Thus, the term "insect" is used not only to include small invertebrate animals belonging to the class "Insecta", but also to other related classes of arthropods, whose members are segmented invertebrates having more or fewer than six legs, such as spiders; mites, ticks and other acanines, centipedes; worms; and the like.

A further understanding of the invention can be had in the following non-limiting Examples. Wherein, unless expressly stated to the contrary, all temperatures and temperature ranges refer to the Centigrade system and the term "ambient" or "room temperature" refers to about 20° C. to about 25° C. The term "percent" refers to weight percent and the term "mol" or "mols" refers to gram mols. The term "equivalent" refers to a quantity of reagent equal in mols, to the mols of the preceding or succeeding reactant recited in that example in terms of finite moles or finite weight or volume. Also, unless expressly stated to the contrary, geometric isomer and racemic mixtures are used as starting materials and correspondingly isomer mixtures are obtained as products.

Compounds prepared in accordance with Examples 1 to 10 below are found in Table I.

EXAMPLES

Example 1

Preparation of Methyl-2,3-dichloro-3-ethylthioacrylate

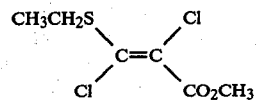

A solution of 270 gms of ethanethiol and 580 ml (419 gms) of triethylamine in 1 liter of methanol was slowly added to 795 gms methyl trichloroacrylate. The addition was exothermic and cooling was required. After addition, the reaction mixture was stirred at room temperature for 18 hours. At this time, an additional 20 gms of ethanethiol was added and the system stirred for an additional 2 hours. The solvent and excess ethanethiol were removed under reduced pressure. The resulting oil was dissolved in methylene chloride. The organic solution was washed with water, dried over magnesium sulfate and filtered. The methylene chloride was removed by stripping to give 860 gms of a brown liquid. The crude product was purified by vacuum distillation to give 600 gms of the methyl-2,3-dichloro-3-ethylthioacrylate (collected at 135°–145° C. at 20 mm Hg).

Example 2

Preparation of
4-Chloro-3-hydroxy-1-methyl-5-ethylthiopyrazole

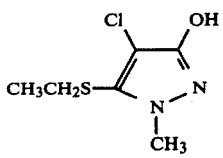

To the solution of methyl-2,3-dichloro-3-ethylthioacrylate (the product of Example 1), 577.1 gms, in 1.5 liters of toluene, was added 370 gms of potassium carbonate followed by slow addition of 123.6 gms of methylhydrazine. The addition was exothermic and cooling of the system was occasionally necessary. When addition of the methylhydrazine was completed, the reaction mixture was allowed to come to room temperature and stirred there for 24 hours. The reaction mixture was then refluxed for an additional 24 hours. The solution was then filtered and the precipitate collected. The toluene filtrate gave ca. 70 gms of the product. The major portion of the product was present in the precipitate as a potassium salt and isolated as follows: The precipitate was added to 2 liters of 10% HCl solution and the product was extracted with methylene chloride. The methylene chloride was concentrated to approximately 500 ml by stripping whereupon the 4-chloro-3-hydroxy-1-methyl-5-ethylthiopyrazole crystallized from solution. The total yield of the final product was 334 gms.

Example 3

Preparation of
Methyl-2,3-dichloro-3-methylthioacrylate

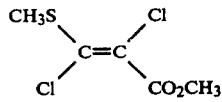

A solution of 4.85 gms (92 mmols) of methanethiol and 9.3 gms (92 mmols) of triethylamine in methanol was slowly added to 17.6 gms (92 mmols) trichloroacrylate with cooling. After addition, the reaction system was stirred at room temperature for about 20 hours. The solvent and excess methanethiol were removed under reduced pressure. Ether was added to the residue (crude product) and the precipitated solvents filtered. The ether was removed under reduced pressure to give an oil. The oil was distilled to give 11.6 gms of a low melting solid (boiling point 125°-150° C. at approximately 50 mm Hg; melting point 27°-30° C.).

Example 4

Preparation of
4-Chloro-3-hydroxy-1-methyl-5-methylthiopyrazole

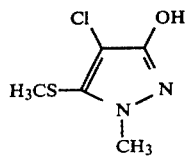

To a stirred solution of 11.6 gms (58 mmols) methyl-2,3-dichloro-3-methylthioacrylate (the product of Example 3) and 8.0 gms (58 mmols) potassium carbonate in 150 mls toluene, 2.1 gms (58 mmols) methylhydrazine were added dropwise. The reaction mixture was heated at 80° C. for about 8 hours. Then an additional 0.5 gm methylhydrazine was added; the resulting mixture was heated to reflux and refluxed for 2 hours. The reaction mixture was cooled and then filtered to remove solids. Stripping of the filtrate, followed by chromatography of the residue on silica gel eluting with ethyl acetate, gave 2.8 gms of the product as a solid with a melting point of 163°-165° C.

Example 5

Preparation of
4,5-Dichloro-3-hydroxy-1-methylpyrazole

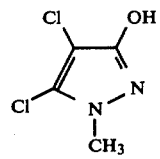

A mixture of 74 gms (0.391 mol) methyl-2,3,3-trichloroacrylate, 18 gms (21 ml) methyl hydrazine and 54 gms (0.391 mol) potassium carbonate in 500 ml toluene was stirred at room temperature for one day, and then heated to reflux for one day. An additional 5 gms methyl hydrazine was then added and the reaction mixture was stirred an additional day at reflux. The reaction mixture was then acidified with dilute hydrochloric acid. At this point, there was a large amount of solid which did not dissolve in either phase. The solids were removed by filtration, resuspended in water and the suspension was filtered again. The solids were air-dried overnight, yielding 60.9 gms of product, melting point 212°-216° C.

Example 6

Preparation of
O,O-Diethyl-O-(4,5-dichloro-1-methylpyrazole-3-yl)-thiophosphate

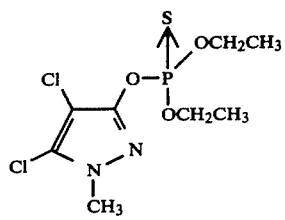

A mixture of 5.7 gms (0.0341 mol) 4,5-dichloro-3-hydroxy-1-methylpyrazole (the product of Example 5), 6.45 gms (0.0341 mol) diethylchlorothiophosphate and 2.35 gms (0.0120 mol) potassium carbonate in 80 ml acetone was stirred at ambient temperature for two hours, gently refluxed for three hours, and then allowed to stand overnight. The mixture was filtered and the solids were washed with acetone. The filtrate and acetone washings were combined and hard-topped to give 10.1 gms of a brown oil.

Elemental analysis for $C_8H_{13}Cl_2N_2O_3PS$ showed: calculated %C 30.11, %H 4.11, and %N 8.78; found %C 30.39, %H 4.24 and %N 9.17.

Example 7

Preparation of O,O-Diethyl-O-(4-chloro-1-methyl-5-ethylthiopyrazole-3-yl)-thiophosphate

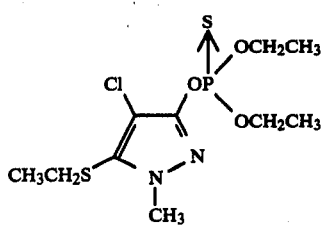

To a stirred mixture of 82.7 gms (0.429 mol) of 4-chloro-3-hydroxy-1-methyl-5-ethylthiopyrazole in 500 ml methyl ethyl ketone, 59 gms (0.429 mol) potassium carbonate was added. To the resulting mixture, 81 gms (0.429 mol) diethylchlorothiophosphate were added slowly. The reaction mixture was stirred at room temperature for two hours, heated to 70° C. and stirred at 70° C. for 4 hours, and then stirred at room temperature overnight.

The reaction mixture was filtered and the filtrate was stripped. The residue was taken up in ether. The ether mixture was then washed 5 times with an ice cold, half-saturated sodium carbonate solution and once with a saturated sodium chloride solution. The ether phase was dried over magnesium sulfate. Stripping of the solvent followed by hard-topping the resulting oil gave 141 gms of product.

Example 8

Preparation of Ethyl-O-ethyl-(4-chloro-1-methyl-5-ethylthiopyrazole-3-yl)-thiophosphonate

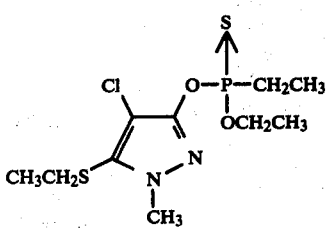

(a) To a stirred mixture of 8.3 gms (0.043 mol) of 4-chloro-3-hydroxy-1-methyl-5-ethylthiopyrazole and 7.0 gms (0.043 mol) ethylphosphonothioic dichloride in 100 ml methylene chloride, 6.0 ml (4.34 g) triethylamine were added dropwise. After a few minutes a precipitate of triethylamine-HCl formed. The mixture was stirred at room temperature for about an hour. After filtering the mixture to remove solids, the mixture containing the product ethyl-O-(4-chloro-1-methyl-5-ethylthiopyrazole-3-yl)-thiophosphinyl chloride was divided into four portions. One portion was used immediately in step (b) without further isolation.

(b) A mixture of one portion (theoretically 3.4 g) of the ethyl-O-(4-chloro-1-methyl-5-ethylthiopyrazole-3-yl)-thiophosphinyl chloride intermediate from step (a), 0.54 gms ethanol, 1.5 ml (1.2 g) triethylamine and additional methylene chloride were stirred for several days (approximately 72 hours) at room temperature. The reaction mixture was washed with water and dried over magnesium sulfate. Stripping of the solvent gave a brown oil. The oil was chromatographed on silica gel, eluting with methylene chloride/hexane 1:1 to give the product, a clear oil.

Elemental analysis for $C_{10}H_{18}ClN_2O_2PS_2$ showed: calculated %C 36.52, %H 5.52, and %N 8.52; found %C 35.84, %H 5.61, and %N 8.65.

Example 9

Preparation of Ethyl-O-ethyl-(4,5-dichloro-1-methylpyrazole-3-yl)-thiophosphonate

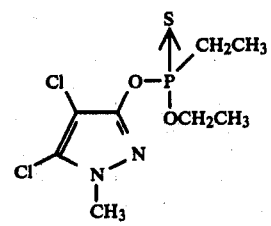

(a) To a stirred mixture of 8 gms (0.048 mol) 4,5-dichloro-3-hydroxy-1-methylpyrazole and 7.8 gms (0.048 mol) ethyl phosphonothioic dichloride in 100 mls methylene chloride, 4.8 gms [6.7 ml (0.048 mol)] triethylamine were added dropwise. The reaction mixture was then stirred for an hour at room temperature. The mixture was then divided into two portions. One portion was used in step (b) without further isolation.

(b) A mixture of one portion of the ethyl-O-(4,5-dichloro-1-methylpyrazole-3-yl)-thiophosphinyl chloride intermediate from step (a), 2.2 gms (3 ml) ethanol and 2.4 gms (3.3 ml) triethylamine and additional methylene chloride were stirred at room temperature for two days. The mixture was washed with water and chromatographed on silica gel, eluting with methylene chloride to give the product, a clear oil.

Elemental analysis for $C_8H_{13}Cl_2N_2O_2PS$ showed: calculated %C 31.69, %H 4.32, and %N 9.24; found %C 30.75, %H 4.49, and %N 8.96.

Example 10

Preparation of Methyl-O-methyl-(4-chloro-1-methyl-5-ethylthiopyrazole-3-yl)-thiophosphonate

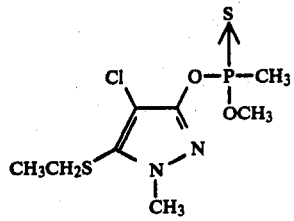

(a) A mixture of 3.2 gms (0.0166 mol) 4-chloro-3-hydroxy-1-methyl-5-ethylthiopyrazole and 2.4 ml (0.0174 mol) triethylamine in about 65 ml methylene chloride was added dropwise with stirring to a mixture of 2.5 gms (0.0166 mol) methylphosphonothioic dichloride in about 10 ml methylene chloride. The combined mixture was stirred for an hour after the addition was complete. The mixture, containing the product, the methyl-O-(4-chloro-1-methyl-5-ethyl-thiopyrazole-3-yl)-thiophosphinyl chloride intermediate was used immediately in step (b) without further isolation.

(b) To the methyl-O-(4-chloro-1-methyl-5-ethylthiopyrazole-3-yl)-thiosphinyl chloride-methylene chloride mixture of step (a), 5 ml methanol were added, followed by 2.5 ml triethylamine. The resulting mixture was stirred several days (approximately 72 hours) at room temperature. The mixture was first washed with water, dried over magnesium sulfate and then stripped to give an oil. The oil was chromatographed on silica gel, eluting with methylene chloride:hexane 1:1 to give 3.5 gms of the product as a light yellow oil.

Elemental analysis for $C_8H_{14}ClN_2O_2S_2P$ showed: calculated %C 31.94, %H 4.69, and %N 9.32; found %C 31.89, %H 5.01, and %N 10.

Compounds made in accordance with Examples 1 to 10 are shown in Table I.

In addition, by following the procedures described in Examples 1 to 10 and using the appropriate starting materials, the following compounds are made:

O,O-Diethyl-O-(4-chloro-1-methyl-5-methylthiopyrazole-3-yl)-phosphate;
O,O-Dimethyl-O-(4-chloro-1-methyl-5-ethylthiopyrazole-3-yl)-phosphate;
O,O-Diisopropyl-O-(4-chloro-1-methyl-5-ethylthiopyrazole-3-yl)-phosphate;
O,O-Di-n-hexyl-O-(4-chloro-1-methyl-5-ethylthiopyrazole)-phosphate;
O,O-Diisopropyl-O-(4-chloro-1-ethyl-5-methylthiopyrazole-3-yl) -phosphate;
O,O-Diethyl-O-(4-chloro-1-methyl-5-ethylthiopyrazole-3-yl)-phosphate;
O,O-Diethyl-O-(4-chloro-1-ethyl-5-n-hexylthiopyrazole-3-yl)-phosphate;
O,O-Dimethyl-O-(4-chloro-1-methyl-5-methylthiopyrazole-3-yl)-phosphate;
O,O-Dimethyl-O-(4-chloro-1-n-propyl-5-isopropylthiopyrazole-3-yl)-phosphate;
O,O-Diethyl-O-(4-chloro-1-n-propyl-5-isopropylthiopyrazole-3-yl)-phosphate;
O,O-Diethyl-O-(4-chloro-1-n-hexyl-5-n-propylthiopyrazole-3-yl)-phosphate;
O,O-Dimethyl-O-(4-chloro-1-n-hexyl-5-n-propylthiopyrazole-3-yl)-phosphate;
O,O-Dimethyl-O-(4,5-dichloro-1-methylpyrazole-3-yl)-phosphate;
O,O-Diethyl-O-(4,5-dichloro-1-methylpyrazole-3-yl)-phosphate;
O-Ethyl,O-methyl-O-(4,5-dichloro-1-methylpyrazole-3-yl)-phosphate;
O-Ethyl,O-isopropyl-O-(4,5-dichloro-1-methyl-pyrazole-3-yl)-phosphate;
O-Ethyl,O-methyl-O-(4,5-dichloro-1-n-propylpyrazole-3-yl)-phosphate;
O,O-Dimethyl-O-(4,5-dichloro-1-ethylpyrazole-3-yl)-phosphate;
O,O-Diisopropyl-O-(4,5-dichloro-1-methylpyrazole-3-yl)-thiophosphate;
O,O-Di-n-hexyl-O-(4,5-dichloro-1-methyl-5-ethylthiopyrazole-3-yl)-thiophosphate;
O,O-Di-n-propyl-O-(4,5-dichloro-1-methylthiopyrazole-3-yl)-thiophosphate;
O,O-Dimethyl-O-(4-chloro-1-methyl-5-ethylthiopyrazole-3-yl)-thiophosphate;
O,O-Di-n-hexyl-O-(4-chloro-1-methyl-5-ethylthiopyrazole-3-yl)-thiophosphate;
O,O-Dimethyl-O-(4-chloro-1-methyl-5-methylthiopyrazole-3-yl)-thiophosphate;
O,O-Diethyl-O-(4-chloro-1-ethyl-5-n-hexylthiopyrazole-3-yl)-thiophosphate;
O,O-Diethyl-O-(4-chloro-1-n-propyl-5-isopropylthiopyrazole-3-yl)-thiophosphate;
O,O-Diethyl-O-(4-chloro-1-n-hexyl-5-n-propylthiopyrazole-3-yl)-thiophosphate;
O-Ethyl,O-methyl-O-(4-chloro-1-n-hexyl-5-n-propylthiopyrazole-3-yl)-thiophosphate;
O-Ethyl,O-methyl-O-(4-chloro-1-methyl-5-methylthiopyrazole-3-yl)-thiophosphate;
O,O-Dimethyl-O-(4,5-dichloro-1-methyl-pyrazole-3-yl)-thiophosphate;
O,O-Diethyl-O-(4,5-dichloro-1-methyl-pyrazole-3-yl)-thiophosphate;
O-Ethyl,O-methyl-O-(4,5-chloro-1-methyl-5-methylthio-pyrazole-3-yl)-thiophosphate;
O-Ethyl,O-isopropyl-O-(4,5-dichloro-1-methyl-pyrazole-3-yl)-thiophosphate;
O-Ethyl,O-Methyl-O-(4,5-dichloro-1-n-propyl-pyrazole-3-yl)-thiophosphate;
Ethyl-O-ethyl-O-(4-chloro-1-methyl-5-methylthiopyrazole-3-yl)-phosphonate;
Methyl-O-methyl-O-(4-chloro-1-methyl-5-ethylthiopyrazole-3-yl)-phosphonate;
Isopropyl-O-isopropyl-O-(4chloro-1-methyl-5-ethylthiopyrazole-3-yl)-phosphonate;
n-Hexyl-O-n-hexyl-O-(4-chloro-1-methyl-5-ethylthiopyrazole-3-yl)-phosphonate;
Ethyl-O-isopropyl-O-(4-chloro-1-ethyl-5-methylthiopyrazole-3-yl)-phosphonate;
Methyl-O-ethyl-O-(4-chloro-1-methyl-5-ethylthiopyrazole-3-yl)-phosphonate;
Ethyl-O-methyl-O-(4-chloro-1-ethyl-5-n-hexylthiopyrazole-3-yl)-phosphonate;
Methyl-O-methyl-O-(4-chloro-1-methyl-5-methylthiopyrazole-3-yl)-phosphonate;
Methyl-O-methyl-O-(4-chloro-1-n-propyl-5-isopropyl-thiopyrazole-3-yl)-phosphonate;
Ethyl-O-ethyl-O-(4-chloro-1-n-propyl-5-isopropylthiopyrazole-3-yl)-phosphonate;
Ethyl-O-ethyl-O-(4-chloro-1-n-hexyl-5-n-propylthiopyrazole-3-yl)-phosphonate;
Methyl-O-methyl-O-(4-chloro-1-n-hexyl-5-n-propylthiopyrazole-3-yl)-phosphonate;
Methyl-O-methyl-O-(4,5-dichloro-1-methylpyrazole-3-yl)-phosphonate;
Ethyl-O-ethyl-O-(4,5-dichloro-1-methyl-3-yl)-phosphonate;
Ethyl-O-methyl-O-(4,5-dichloro-1-methylpyrazole-3-yl)-phosphonate;
Ethyl-O-isopropyl-O-(4,5-dichloro-1-methylpyrazole-3-yl)-phosphonate;
Methyl-O-ethyl-O-(4,5-dichloro-1-n-propylpyrazole-3-yl)-phosphonate;
Methyl-O-methyl-O-(4-chloro-1-ethyl-5-n-butylthiopyrazole-3-yl)-thiophosphonate;
Isopropyl,O-isopropyl-O-(4-chloro-1-methyl-5-ethylthiopyrazole-3-yl)-thiophosphonate;
n-Hexyl-O-n-hexyl-O-(4-chloro-1-methyl-5-ethylthiopyrazole-3-yl)-thiophosphonate;
n-Propyl-O-n-propyl-O-(4-chloro-1-methyl-5-methylthiopyrazole-3-yl)-thiophosphonate;
Methyl-O-methyl-O-(4-chloro-1-methyl-5-methylthiopyrazole-3-yl)-thiophosphonate;
Methyl-O-isopropyl-O-(4-chloro-1-methyl-5-methylthiopyrazole-3-yl)-thiophosphonate;

Ethyl-O-ethyl-O-(4-chloro-1-ethyl-5-n-hexylthi-
opyrazole-3-yl)-thiophosphonate;
Ethyl-O-ethyl-O-(4-chloro-1-n-propyl-5-isopropylthi-
opyrazole-3-yl)-thiophosphonate;
Ethyl-O-ethyl-O-(4-chloro-1-n-hexyl-5-n-propylthi-
opyrazole-3-yl)-thiophosphonate;
Ethyl-O-methyl-O-(4-chloro-1-n-hexyl-5-n-propylthi-
opyrazole-3-yl)-thiophosphonate;
Ethyl-O-methyl-O-(4-chloro-1-methyl-5-methylthi-
opyrazole-3-yl)-thiophosphonate;
Methyl-O-ethyl-O-(4-chloro-1-methyl-5-methylthi-
opyrazole-3-yl)-thiophosphonate;
Methyl-O-ethyl-O-(4-chloro-1-methyl-5-ethylthi-
opyrazole-3-yl)-thiophosphonate;
Ethyl-O-methyl-O-(4-chloro-1-methyl-5-ethylthi-
opyrazole-3-yl)-thiophosphonate;
Methyl-O-methyl-O-(4,5-dichloro-1-methylpyrazole-3-
yl)-thiophosphonate;
Ethyl-O-ethyl-O-(4,5-dichloro-1-methyl-pyrazole-3-
yl)-thiophosphonate;
Ethyl-O-methyl-O-(4,5-dichloro-1-methylpyrazole-3-
yl)-thiophosphonate;
Ethyl-O-isopropyl-O-(4,5-dichloro-1-methylpyrazole-
3-yl)-dithiophosphonate;
Methyl-O-ethyl-O-(4,5-dichloro-1-n-propylpyrazole-3-
yl)-thiophosphonate; and
Methyl-O-isopropyl-O-(4,5-dichloro-1-methylpyrazole-
3-yl)-thiophosphonate.

Note: The Rank of the candidate toxicants reported in Tables III to VI was based on a compression of the percent controls over the dosage range and visual observation when the test was read.

Example A

Cabbage Looper Control I

The compounds of the invention were tested for their insecticidal activity against Cabbage Looper [*Trichoplusia ni* (Hubner)]. An acetone solution of the candidate toxicant containing a small amount of nonionic emulsifier was diluted with water to 500 ppm. Excised cucumber leaves were dipped in the toxicant solution and the solution on the leaves was allowed to dry. The treated leaves were then infested with Cabbage Looper larvae (mid-third stage). Mortality readings were taken after 24 hours. The results are tabulated in Table II in terms of percent control.

Example B

Cabbage Looper Control II

The compounds of this invention were tested for their insecticidal activity against Cabbage Looper larvae [*Trichoplusia ni* (Hubner)] at range of concentrations of candidate toxicant (compound).

An acetone solution of 50 mgs candidate toxicant in 10 ml acetone with a small amount nonionic emulsifier (ORTHO X-77 nonionic spreader) was diluted with distilled water to give a concentration of 500 ppm. The 500 ppm solution was further diluted with water to give solutions of 200 ppm, 80 ppm and 32 ppm candidate toxicant, respectively.

Excised cucumber leaves were dipped in toxicant solution and the solution on the leaves allowed to dry. The treated leaves were then infested with Cabbage Looper larvae (mid-third stage) of uniform size (4 replicas per concentration). The infested leaves were incubated at about 70° to 75° F. Mortality readings were taken after 24 and 48 hours. The results, as percent control, are tabulated in Table III.

Example C

Housefly

The compounds of this invention were tested for their activity against houseflies (*Musca domestica* Linnaeus) at a range of concentrations of candidate toxicant.

An acetone solution of 2 mg candidate toxicant in 20 ml acetone was made to give a starting concentration of 100 ppm. The 100 ppm solution was diluted further with acetone to give solutions of 40 ppm, 16 ppm and 6.4 ppm candidate toxicant, respectively.

A random mixture of anesthetized male and female 3- to 5-day old houseflies were placed in a container and sprayed with a microsprayer (atomizer) which was calibrated to deliver 70 microliters (about 55 mg) of candidate toxicant solution (4 replicates per toxicant dose). Mortality counts were made 24 hours after treatment. The percent control was calculated from the average of the exact mortality counts in the four replicates and is tabulated in Table IV.

Example D

Cotton Aphids

The compounds of this invention were tested for insecticidal activity against cotton aphids (*Aphis gossypii* Glover) at a range of concentrations.

An acetone solution of 10 mgms candidate toxicant in 10 ml acetone was added to 90 ml water containing a small amount nonionic emulsifer (ORTHO X-77 nonionic spreader) to give a starting solution of 100 ppm. The 100 ppm solution was diluted with water to obtain the test solutions containing 10 ppm, 4 ppm, 1.6 ppm and 0.64 ppm candidate toxicant, respectively.

Cucumber leaves infested with cotton aphids were dipped in toxicant solution (4 replicates per toxicant concentration). Infested leaves dipped in water plus emulsifier served as check treatments. Excess solution was drained from the leaves and the solution on the leaves was allowed to dry. The infested leaves were incubated at about 75° F. for 24 hours.

Mortality readings were taken at 24 hours by locating a field of 20 aphids on a treated leaf and recording the number dead which were used to calculate the average kill and percent control. The results expressed as % control are tabulated in Table V.

Example E

Alfalfa Weevil

The compounds of this invention were tested for their insecticidal activity against Alfalfa Weevil (*Hypera brunneipennis* Boheman) at a range of concentrations of candidate toxicant.

An acetone solution of candidate toxicant in acetone was made to give a starting concentration of 100 ppm. The 100 ppm solution was diluted further with acetone to give solutions of 40 ppm, 16 ppm and 6.4 ppm candidate toxicant, respectively.

Anesthetized Alfalfa Weevils were placed in a container and sprayed with a microsprayer which was calibrated to deliver 70 microliters (about 55 mg) of candidate solution (4 replicates per toxicant dose). Mortality counts were made 24 hours after treatment. The percent control was calculated from the average of the exact mortality counts in the four replicates and is tabulated in Table VI.

TABLE I

Compounds of the Formula

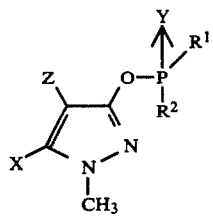

| Compound No. | X | Z | Y | R¹ | R² | Physical State | %C Calc | %C Fd. | %H Calc | %H Fd. | %N Calc | %N Fd. |
|---|---|---|---|---|---|---|---|---|---|---|---|---|
| 1  39046 | —SCH$_2$CH$_3$ | —Cl | S | —OCH$_2$CH$_3$ | —CH$_2$CH$_3$ | Clear oil | 36.52 | 35.84 | 5.52 | 5.61 | 8.52 | 8.65 |
| 2  33055 | —SCH$_2$CH$_3$ | —Cl | S | —OCH$_2$CH$_3$ | —OCH$_2$CH$_3$ | oil | 34.83 | 33.9 | 5.26 | 5.22 | 8.12 | 7.75 |
| 3  41710 | —SCH$_2$CH$_3$ | —Cl | S | —OCH$_3$ | —CH$_3$ | Light yellow oil | 31.94 | 31.89 | 4.69 | 5.01 | 9.32 | 10 |
| 4  40425 | —Cl | —Cl | S | —OCH$_2$CH$_3$ | —CH$_2$CH$_3$ | clear oil | 31.69 | 30.75 | 4.32 | 4.49 | 9.24 | 8.96 |
| 5  29176 | —Cl | —Cl | S | —OCH$_2$CH$_3$ | —OCH$_2$CH$_3$ | brown oil | 30.11 | 30.39 | 4.11 | 4.24 | 8.78 | 9.17 |
| 6  33268 | —SCH$_2$CH$_3$ | —Cl | O | —OCH$_2$CH$_3$ | —OCH$_2$CH$_3$ | brown oil | 36.53 | 35.59 | 5.52 | 5.7 | 8.52 | 7.92 |
| 7  29416 | —Cl | —Cl | O | —OCH$_2$CH$_3$ | —OCH$_2$CH$_3$ | straw oil | 31.70 | 31.27 | 4.32 | 3.98 | 9.24 | 9.8 |
| 8  33272 | —SCH$_3$ | —Cl | S | —OCH$_2$CH$_3$ | —OCH$_2$CH$_3$ | light brown oil | 32.67 | 31.39 | 4.88 | 4.83 | 8.47 | 8.11 |
| 11C 37357 | —SCH$_2$CH$_3$ | H | S | —OCH$_2$CH$_3$ | —OCH$_2$CH$_3$ | light yellow oil | 38.7 | 38.71 | 6.18 | 6.16 | 9.03 | 9.13 |
| 12C 41590 | —SCH$_2$CH$_3$ | H | S | —OCH$_2$CH$_3$ | —CH$_2$CH$_3$ | | | | | | | |
| 13C 41647 | —SCH$_2$CH$_3$ | CN | S | —OCH$_2$CH$_3$ | —OCH$_2$CH$_3$ | | | | | | | |
| 14C 41714 | —SCH$_2$CH$_3$ | CN | S | —OCH$_2$CH$_3$ | —CH$_2$CH$_3$ | | | | | | | |

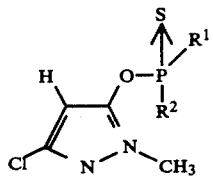

| | | | R¹ | R² |
|---|---|---|---|---|
| 15C 41484 | | | —OCH$_2$CH$_3$ | —OCH$_2$CH$_3$ |
| 16C 41485 | | | —OCH$_2$CH$_3$ | —CH$_2$CH$_3$ |

TABLE II

Cabbage Looper Larvae I

| Compound No. | % C |
|---|---|
| 1  39046 | 100 |
| 2  33055 | 90 |
| 3  41710 | 100 |
| 4  40425 | 100 |
| 5  29176 | 60 |
| 6  33268 | 100 |

TABLE II-continued

Cabbage Looper Larvae I

| Compound No. | % C |
|---|---|
| 7  29416 | 100 |
| 8  33272 | 100 |
| 11C 37357 | 0 |
| 12C 41590 | 22 |
| 13C 41647 | 0 |
| 14C 41714 | 0 |
| 15C 41484 | 100 |
| 16C 41485 | 80 |

TABLE III

Cabbage Looper Larvae II

| Compound No. | 24-hour % C at Dose (ppm) 500 | 200 | 80 | 32 | Rank | 48-hour % C at Dose (ppm) 500 | 200 | 80 | 32 | Rank |
|---|---|---|---|---|---|---|---|---|---|---|
| 1  39046 | 100 | 100 | 100 | 100 | 1 | 100 | 100 | 100 | 100 | 1 |
| 2  33055 | 100 | 93 | 33 | 27 | 5 | 100 | 100 | 62 | 40 | 3 |
| 3  41710 | 100 | 100 | 87 | 40 | 4 | 100 | 100 | 100 | 47 | 2 |
| 4  40425 | 100 | 100 | 100 | 100 | 1 | 100 | 100 | 100 | 100 | 1 |
| 11C 37357 | 47 | 20 | 20 | 13 | 7 | 47 | 27 | 13 | 13 | 7 |
| 12C 41590 | 27 | 27 | 13 | 40 | 7 | 53 | 33 | 13 | 40 | 6 |

TABLE III-continued

| Compound | | Cabbage Looper Larvae II | | | | | | | | |
|---|---|---|---|---|---|---|---|---|---|---|
| | | 24-hour % C at Dose (ppm) | | | | | 48-hour % C at Dose (ppm) | | | |
| No. | | 500 | 200 | 80 | 32 | Rank | 500 | 200 | 80 | 32 | Rank |
| 13C | 41647 | 7 | 7 | 0 | 0 | 8 | 0 | 7 | 0 | 6 | 8 |
| 14C | 41714 | 93 | 40 | 13 | 0 | 6 | 100 | 67 | 27 | 7 | 4 |
| 15C | 41484 | 100 | 100 | 100 | 100 | 1 | 100 | 100 | 100 | 100 | 1 |
| 16C | 41485 | 100 | 100 | 100 | 100 | 1 | 100 | 100 | 100 | 100 | 1 |

TABLE VI

| | House Fly | | | | |
|---|---|---|---|---|---|
| | % Control at ppm | | | | |
| Compound No. | 100 | 40 | 16 | 6.4 | Rank |
| 1 39046 | 86 | 24 | 9 | 0 | 4 |
| 2 33055 | 34 | 14 | 8 | 3 | 7 |
| 3 41710 | 91 | 21 | 1 | 4 | 5 |
| 4 40425 | 100 | 79 | 19 | 8 | 2 |
| 11C 37357 | 30 | 10 | 11 | 6 | 8 |
| 12C 41590 | 66 | 8 | 1 | 1 | 6 |
| 13C 41647 | 5 | 1 | 1 | 0 | 13 |
| 14C 41714 | 9 | 1 | 3 | 4 | 12 |
| 15C 41484 | 76 | 39 | 5 | 3 | 3 |
| 16C 41485 | 100 | 95 | 36 | 0 | 1 |

TABLE V

| | Cotton Aphid | | | | |
|---|---|---|---|---|---|
| | % Control at ppm | | | | |
| Compound No. | 10 | 4 | 1.6 | 0.64 | Rank |
| 1 | 100 | 100 | 100 | 96 | 3 |
| 2 | 100 | 100 | 100 | 79 | 6 |
| 3 | 100 | 100 | 100 | 99 | 2 |
| 4 | 100 | 100 | 100 | 89 | 5 |
| 11C | 100 | 100 | 95 | 51 | 10 |
| 12C | 100 | 100 | 100 | 91 | 4 |
| 13C | 100 | 100 | 100 | 83 | 7 |
| 14C | 100 | 100 | 98 | 93 | 5 |
| 15C | 100 | 100 | 100 | 99 | 2 |
| 16C | 100 | 100 | 100 | 100 | 1 |

TABLE VI

| | Alfalfa Weevil | | | | |
|---|---|---|---|---|---|
| | % Control at ppm | | | | |
| Compound No. | 100 | 40 | 16 | 6.4 | Rank |
| 1 | 100 | 70 | 10 | 0 | 2 |
| 2 | 100 | 25 | 0 | 0 | 4 |
| 3 | 95 | 85 | 20 | 5 | 2 |
| 4 | 25 | 5 | 5 | 0 | 7 |
| 11C | 100 | 50 | 0 | 10 | 3 |
| 12C | 100 | 100 | 5 | 0 | 1 |
| 13C | 25 | 10 | 0 | 0 | 7 |
| 14C | 75 | 0 | 0 | 10 | 6 |
| 15C | 100 | 60 | 10 | 5 | 2 |
| 16C | 100 | 95 | 30 | 5 | 1 |

What is claimed is:

1. A compound of the formula

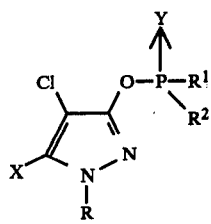

wherein R is lower alkyl; $R^1$ is lower alkoxy; $R^2$ is lower alkyl or lower alkoxy; X is chloro or the group $—SR^3$ wherein $R^3$ is lower alkyl; and Y is sulfur or oxygen.

2. A compound of the formula defined in claim 1 wherein Y is sulfur.

3. A compound of the formula defined in claim 1 wherein $R^3$ is ethyl.

4. A compound of the formula defined in claim 3 wherein Y is sulfur.

5. A compound of the formula defined in claim 4 wherein R is methyl.

6. A compound of the formula defined in claim 5 wherein $R^2$ is methoxy and $R^2$ is methyl.

7. A compound of the formula defined in claim 6 wherein X is $—SR^3$.

8. A compound of the formula defined in claim 5 wherein $R^1$ is ethoxy.

9. A compound of the formula defined in claim 8 wherein $R^2$ is ethyl and X is chloro.

10. A compound of the formula defined in claim 8 wherein X is $—SR^3$.

11. A compound of the formula defined in claim 10 wherein $R^2$ is ethoxy.

12. A compound of the formula defined in claim 10 wherein $R^2$ is ethyl.

13. A method of killing insects which comprises contacting said insect or its habitat with an insecticidally effective amount of a compound of the formula defined in claim 1.

14. A method of killing insects which comprises contacting said insect or its habitat with an insecticidally effective amount of a compound of the formula defined in claim 3.

15. A method of killing insects which comprises contacting said insect or its habitat with an insecticidally effective amount of a compound of the formula defined in claim 5.

16. A method of killing insects which comprises contacting said insect or its habitat with an insecticidally effective amount of a compound of the formula defined in claim 7.

17. A method of killing insects which comprises contacting said insect or its habitat with an insecticidally effective amount of a compound of the formula defined in claim 9.

18. A method of killing insects which comprises contacting said insect or its habitat with an insecticidally effective amount of a compound of the formula defined in claim 11.

19. An insecticidal composition which comprises a biologically inert carrier and an insecticidally effective amount of a compound of the formula defined in claim 1.

20. An insecticidal composition which comprises a biologically inert carrier and an insecticidally effective amount of a compound of the formula defined in claim 3.

21. An insecticidal composition which comprises a biologically inert carrier and an insecticidally effective amount of a compound of the formula defined in claim 5.

22. An insecticidal composition which comprises a biologically inert carrier and an insecticidally effective amount of a compound of the formula defined in claim 7.

23. An insecticidal composition which comprises a biologically inert carrier and an insecticidally effective amount of a compound of the formula defined in claim 9.

24. An insecticidal composition which comprises a biologically inert carrier and an insecticidally effective amount of a compound of the formula defined in claim 11.

* * * * *